(12) United States Patent
Lacroix et al.

(10) Patent No.: US 11,219,649 B2
(45) Date of Patent: Jan. 11, 2022

(54) CONSORTIA OF LIVING BACTERIA USEFUL FOR TREATMENT OF MICROBIOME DYSBIOSIS

(71) Applicants: ETH Zurich, Zürich (CH); Universität Zürich, Zürich (CH)

(72) Inventors: Christophe Lacroix, Kilchberg (CH); Tomas De Wouters, Zürich (CH); Gerhard Rogler, Zürich (CH); Christophe Chassard, Lempdes (FR); Laura Berchtold, Stalden (CH); Fabienne Kurt, Zürich (CH); Michael Martin Scharl, Aesch (CH); Marianne Rebecca Spalinger, Staufen (CH); Markus Reichlin, Winterthur (CH); Florian Nils Rosenthal, Zürich (CH); Marco Meola, Affoltern am Albis (CH)

(73) Assignees: ETH Zurich, Zürich (CH); UNIVERSITÄT ZÜRICH, Zürich (CH)

( * ) Notice: Subject to any disclaimer, the term of this patent is extended or adjusted under 35 U.S.C. 154(b) by 191 days.

(21) Appl. No.: 16/604,236

(22) PCT Filed: Apr. 12, 2018

(86) PCT No.: PCT/EP2018/059378
§ 371 (c)(1),
(2) Date: Oct. 10, 2019

(87) PCT Pub. No.: WO2018/189284
PCT Pub. Date: Oct. 18, 2018

(65) Prior Publication Data
US 2020/0276250 A1      Sep. 3, 2020

(30) Foreign Application Priority Data
Apr. 12, 2017      (EP) .................................... 17166375

(51) Int. Cl.
*A61K 35/745*      (2015.01)
*A61P 1/00*      (2006.01)
(Continued)

(52) U.S. Cl.
CPC .......... *A61K 35/745* (2013.01); *A61K 35/742* (2013.01); *A61K 35/747* (2013.01);
(Continued)

(58) Field of Classification Search
CPC .. A61K 2300/00; A61K 35/74; A61K 35/742; A61K 35/744; A61K 35/747; A61K 9/0053; A61K 35/745; A61K 9/0031; A61K 31/715; A61K 35/741; A61K 2035/115; A61K 31/7004; A61K 31/7016; A61K 35/39; A61K 38/46; A61K 9/19; A61K 31/19; A61K 38/18; A61K 38/19; A61K 38/50; A61K 39/3955; A61K 45/06; A61K 9/4891; A61K 31/716; A61K 31/736; A61K 47/26; A61K 9/0029; A61K 9/0095; A61K 9/2086; A61K 2035/11; A61K 2039/507; A61K 2039/521; A61K 2039/522; A61K 2039/55594; A61K 2039/585; A61K 31/215; A61K 31/352; A61K 35/17; A61K 39/02; A61K 39/39; A61K 9/00; A61K 9/4808; A61K 9/4875; A61K 35/37; A61K 9/48; A61K 9/4816; A61K 38/13; A61P 1/00; A61P 43/00; A61P 29/00; A61P 37/00; A61P 13/12; A61P 1/12;
(Continued)

(56) References Cited

U.S. PATENT DOCUMENTS 8,021,659 B2 * 9/2011 Naidu ..................... A61K 45/06
424/94.1
9,788,563 B2 * 10/2017 Fang ......................... A23L 2/60
(Continued)

FOREIGN PATENT DOCUMENTS

WO      2012142605 A1      10/2012
WO      2013037068 A1      3/2013
(Continued)

OTHER PUBLICATIONS

Roth, Emmanuelle, et al., "Facultative Anaerobic Halophilic and Alkaliphilic Bacteria Isolated from a Natural Smear Ecosystem Inhibitgrowth in Early Ripening Stages," International Journal of Food Microbiology, 147(1): pp. 26-32 (Feb. 2011).
(Continued)

*Primary Examiner* — Deborah K Ware
(74) *Attorney, Agent, or Firm* — Elmore Patent Law Group, P.C.; Joseph Zucchero; Carolyn Elmore

(57) ABSTRACT

The present invention relates to novel compositions comprising specific consortia of living bacteria strains; to the manufacturing of such compositions, particularly by co-cultivation; and to the use of such compositions in pharmaceutical applications, such as the treatment of diseases associated with intestinal microbiota dysbiosis, particularly intestinal infections such as CDI (*Clostridium difficile* infection) and IBD (Inflammatory bowel diseases). When compared to the traditional FMT therapy ( ) the inventive compositions ( ) are more efficient and safer as demonstrated on an acute colitis model and therefore more appropriate for therapeutic use.

Figure 1:
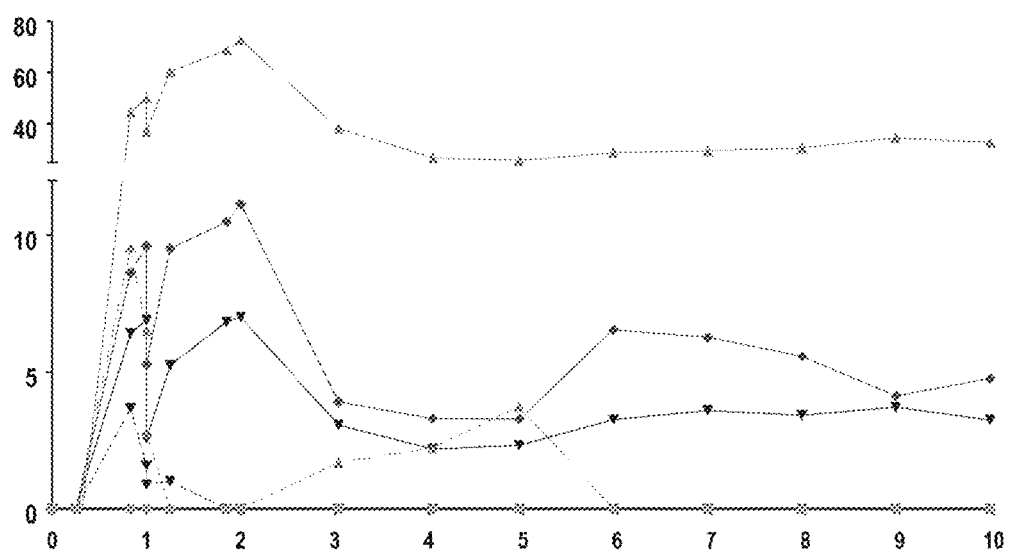

18 Claims, 8 Drawing Sheets
Specification includes a Sequence Listing.

(51) Int. Cl.
*A61K 35/742* (2015.01)
*A61K 35/747* (2015.01)
*A61K 9/00* (2006.01)

(52) U.S. Cl.
CPC .............. *A61P 1/00* (2018.01); *A61K 9/0031* (2013.01); *A61K 9/0053* (2013.01)

(58) Field of Classification Search
CPC .... A61P 1/16; A61P 35/00; A61P 3/00; A61P 9/00; A61P 31/04; A61P 1/04; A61P 1/14; A61P 31/00; A61P 37/04; A61P 3/04; A61P 3/10; Y02A 50/30; Y02A 50/473; A23L 33/135; A23L 5/00; A23L 33/127; C12N 1/20; A01N 43/16; C07H 1/00; C07H 3/06; C07K 16/2818; C07K 16/2827; C08B 37/006; C12Q 1/04; C12Q 1/06; C12Q 1/18; C12Q 1/34; C12Q 1/689; C12Y 305/01024; G01N 24/088; G01N 33/56911; A23P 10/30; A23V 2002/00; C12R 1/00

See application file for complete search history.

(56) References Cited

U.S. PATENT DOCUMENTS

| | | | |
|---|---|---|---|
| 2016/0000838 | A1 | 1/2016 | Harmsen et al. |
| 2016/0243175 | A1 | 8/2016 | Bushman et al. |

FOREIGN PATENT DOCUMENTS

| | | | |
|---|---|---|---|
| WO | 2013053836 | A1 | 4/2013 |
| WO | 2014110685 | A1 | 7/2014 |
| WO | 2014121298 | A2 | 8/2014 |
| WO | 2014145958 | A2 | 9/2014 |
| WO | 2015051323 | A1 | 4/2015 |
| WO | 2016086161 | A1 | 6/2016 |
| WO | 2016201114 | A1 | 12/2016 |

OTHER PUBLICATIONS

Berner, A.Z., et al., "Novel Polyfermentor Intestinal Model (PolyFermS) for Controlled Ecological Studies: Validation and Effect of pH," PLOS One, 8(10), Oct. 2013.

Bryant, M.P., "Commentary on the Hungate Technique for Culture of Anaerobic Bacteria, The American Journal of Clinical Nutrition," pp. 1324-1328, Dec. 1972.

Chassard, C., et al., "Carbohydrates and the Human Gut Microbiota," Current Opinion Clinical Nutrition Metab Care, 16: pp. 453-460 (2013).

Duncan, S.H., et al., "Growth Requirements and Fermentation Products of Fusobacterium Prausnitzii, and a Proposal to Reclassify it as Faecalibacterium Prausnitzii gen, Nov., comb, Nov." International Journal of Systematic and Evolutionary Microbiology, vol. 52, pp. 2141-2146 (2002).

Kaufmann, P., et al., "Identification and Quantification of Bifidobacterium Species Isolated from Food with Genus-Specific 16S rRNA-Targeted Probes by Colony Hybridization and PCR," Applied and Environmental Microbiology, 63 (4): pp. 1268-1273 (1997).

Lane, D.J., "Nucleic Acid Techniques in Bacterial Systematics," RNA Sequencing, pp. 131-133.

Leclerc, M., et al., "H2CO2 Metabolism in Acetogenic Bacteria Isolated From the Human Colon," Anaerobe, vol. 3, pp. 307-315 (1997).

Lopes-Siles, M., et al.,"Cultured Representatives of Two Major Phylogroups of Human Colonic Faecalibacterium Prausnitzii Can Utilize Pectin, Uronic Acids, and Host-Derived Substrates for Growth," Applied and Environmental Microbiology, pp. 420-428, Jan. 2012.

Maeda, H., et al., "Quantitative Real-Time PCR Using TaqMan and SYBR Green for Actinobacillus Actinomycetemcomitans, Porphyromonas Gingivalis, Prevotella intermedia, tetQ Gene and Total Bacteria," FEMS Immunology and Medical Microbiology, vol. 39, pp. 81-86 (2003).

Mosoni, P., et al., "Quantification by Real-Time PCR of Cellulolytic Bacteria in the Rumen of Sheep after Supplementation of a Forage Diet with Readily Fermentable Carbohydrates: Effect of a Yeast Additive," Journal of Applied Microbiology, vol. 103, pp. 2676-2685 (2007).

Muyzer, G., et al., "Profiling of Complex Microbial Populations by Denaturing Gradient Gel Electrophoresis Analysis of Polymerase Chain Reaction-Amplified Genes Coding for 16S rRNA," Applied and Environmental Microbiology, 59 (3): pp. 695-700 (Mar. 1993).

Ritari, J., et al., "Improved Taxonomic Assignment of Human Intestinal 16S rRNA Sequences by a Dedicated Reference Database," BMC Genomics, 16: 1056 (2015).

Wang, Rong-Fu, et al., "PCR Detection and Quantitation of Predominant Anaerobic Bacteria in Human and Animal Fecal Samples," Applied and Environmental Microbiology, 62(4): pp. 1242-1247 (Apr. 1996).

* cited by examiner

```
                         SEQUENCE LISTING

<160> NUMBER OF SEQ ID NOS: 30

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
cgcgtgaagg atgaaggttt tc                                            22

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
tcagttaaag cccagcaggc                                               20

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
cgcggtaaaa cgtaggtcac a                                             21

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer

<400> SEQUENCE: 4
ctgggacgtt gtttctgagt tt                                            22

<210> SEQ ID NO 5
<211> LENGTH: 22
<212> TYPE: DNA
<213> ORGANISM: Artificial Sequence
<220> FEATURE:
<223> OTHER INFORMATION: Synthetic Primer

<400> SEQUENCE: 5
ggaatcttcc acaatggacg ca                                            22
```

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
catggagttc cactgtcctc tt                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
ggaatcttcc acaatggacg ca                                              22

<210> SEQ ID NO 8
<211> LENGTH: 17
<212> TYPE: DNA
<213> ORGANISM: Artificial Sequence
<220> FEATURE:
<223> OTHER INFORMATION: Synthetic Primer

<400> SEQUENCE: 8
accacctgtg aacccgc                                                    17

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer

<400> SEQUENCE: 9
gcactccacc tggggagt                                                   18

<210> SEQ ID NO 10
<211> LENGTH: 22
<212> TYPE: DNA
<213> ORGANISM: Artificial Sequence
<220> FEATURE:
<223> OTHER INFORMATION: Synthetic Primer

<400> SEQUENCE: 10
caaccttcct ccgggttatc ca                                              22

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
ggcttgctgg acaaatactg                                                 20

<210> SEQ ID NO 12
<211> LENGTH: 20
<212> TYPE: DNA
<213> ORGANISM: Artificial Sequence
<220> FEATURE:

<223> OTHER INFORMATION: Synthetic Primer

<400> SEQUENCE: 12
ctaggctcgt cagaaggatg                                        20

<210> SEQ ID NO 13
<211> LENGTH: 18
<212> TYPE: DNA
<213> ORGANISM: Artificial Sequence
<220> FEATURE:
<223> OTHER INFORMATION: Synthetic Primer

<400> SEQUENCE: 13
ggtaggggag ggtggaac                                          18

<210> SEQ ID NO 14
<211> LENGTH: 17
<212> TYPE: DNA
<213> ORGANISM: Artificial Sequence
<220> FEATURE:
<223> OTHER INFORMATION: Primer

<400> SEQUENCE: 14
gcggtcccgc gtgggtt                                           17

<210> SEQ ID NO 15
<211> LENGTH: 22
<212> TYPE: DNA
<213> ORGANISM: Artificial Sequence
<220> FEATURE:
<223> OTHER INFORMATION: Synthetic Primer

<400> SEQUENCE: 15
ggagtgctaa taccggatgt ga                                     22

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
ccgtggcttc ctcgtttact                                        20

<210> SEQ ID NO 17
<211> LENGTH: 24
<212> TYPE: DNA
<213> ORGANISM: Artificial Sequence
<220> FEATURE:
<223> OTHER INFORMATION: Synthetic Primer

<400> SEQUENCE: 17
cgtgaaggaa gaagtatctc ggta                                   24

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer

<400> SEQUENCE: 18
tcagttaccg tccagcaggc c                                      21

```
<210> SEQ ID NO 19
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: S is G or C
<220> FEATURE:
<221> NAME/KEY: misc_feature
<222> LOCATION: (9)..(9)
<223> OTHER INFORMATION: Y is C or T
<220> FEATURE:
<221> NAME/KEY: misc_feature
<222> LOCATION: (12)..(12)
<223> OTHER INFORMATION: Y is C or T

<400> SEQUENCE: 19
gtgstgcayg gytgtcgtca                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (6)..(6)
<223> OTHER INFORMATION: R is A or G
<220> FEATURE:
<221> NAME/KEY: misc_feature
<222> LOCATION: (12)..(12)
<223> OTHER INFORMATION: R is A or G

<400> SEQUENCE: 20
acgtcrtccc crccttcctc                                              20

<210> SEQ ID NO 21
<211> LENGTH: 17
<212> TYPE: DNA
<213> ORGANISM: Artificial Sequence
<220> FEATURE:
<223> OTHER INFORMATION: Synthetic Primer

<400> SEQUENCE: 21
attaccgcgg ctgctgg                                                 17

<210> SEQ ID NO 22
<211> LENGTH: 15
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (14)..(14)
<223> OTHER INFORMATION: R is A or G

<400> SEQUENCE: 22
acgggcggtg tgtrc                                                   15

<210> SEQ ID NO 23
<211> LENGTH: 21
<212> TYPE: DNA
<213> ORGANISM: Artificial Sequence
<220> FEATURE:
<223> OTHER INFORMATION: Synthetic Primer
<220> FEATURE:
```

```
<221> NAME/KEY: misc_feature
<222> LOCATION: (9)..(9)
<223> OTHER INFORMATION: n is a, c, g, or t

<400> SEQUENCE: 23
cgggtgctnc ccactttcat g                                              21

<210> SEQ ID NO 24
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (2)..(2)
<223> OTHER INFORMATION: n is a, c, g, or t

<400> SEQUENCE: 24
gntaccttgt tacgactt                                                  18

<210> SEQ ID NO 25
<211> LENGTH: 22
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (6)..(6)
<223> OTHER INFORMATION: Y is C or T

<400> SEQUENCE: 25
tacggytacc ttgttacgac tt                                             22

<210> SEQ ID NO 26
<211> LENGTH: 17
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (10)..(10)
<223> OTHER INFORMATION: W is A or T
<220> FEATURE:
<221> NAME/KEY: misc_feature
<222> LOCATION: (15)..(15)
<223> OTHER INFORMATION: R is A or G

<400> SEQUENCE: 26
aaggaggtgw tccarcc                                                   17

<210> SEQ ID NO 27
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (12)..(12)
<223> OTHER INFORMATION: M is A or C

<400> SEQUENCE: 27
agagtttgat cmtggctc                                                  18

<210> SEQ ID NO 28
<211> LENGTH: 21
```

```
<212> TYPE: DNA
<213> ORGANISM: Artificial Sequence
<220> FEATURE:
<223> OTHER INFORMATION: Synthetic Primer

<400> SEQUENCE: 28
gattctggct caggatgaac g                                        21

<210> SEQ ID NO 29
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (12)..(12)
<223> OTHER INFORMATION: M is A or C

<400> SEQUENCE: 29
agagtttgat cmtggctcag                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
ccagcagccg cggtaatacg                                          20
```

CONSORTIA OF LIVING BACTERIA USEFUL FOR TREATMENT OF MICROBIOME DYSBIOSIS

RELATED APPLICATIONS

This application is a US National stage entry of International Application No. PCT/EP2018/059378, which designated the United States and was filed on Apr. 12, 2018, published in English. This application claims priority under 35 U.S.C. § 119 or 365 to European, Application No. 17166375.0, filed Apr. 12, 2017. The entire teachings of the above applications are incorporated herein by reference.

The present invention relates to novel compositions comprising specific consortia of living bacteria strains; to the manufacturing of such compositions, particularly by co-cultivation; and to the use of such compositions in pharmaceutical applications, such as the treatment of diseases associated with intestinal microbiota dysbiosis, particularly intestinal infections such as CDI (*Clostridium difficile* infection) and IBD (Inflammatory bowel diseases). It was found that the inventive compositions are more efficient and safer in the treatment of dysbiosis and intestinal inflammation, when compared to the traditional FMT therapy. Accordingly, these compositions are suitable for the treatment of a broad range of diseases and disorders, particularly CDI and IBD.

Fecal microbiota transplant (FMT) or the transfer of fresh fecal material from a donor to the patient, is known as an effective treatment in last resort cases of recurrent CDI, with striking efficacy of over 90% and fast recovery of bowel function. However, FMT bears significant risks to the patient, due to the unknown compatibility of the patient with the donor's microbiota, resulting in different immune reactions, implantation efficacy and efficacy of the treatment.

WO2013/053836 describes compositions comprising anaerobically cultivated human intestinal microbiota and their use in the treatment of diseases located in the GI system. However, the proposed consortia are of human origin, complex, and non-defined, therefore, bearing the same risks as discussed above in the context of FMT.

WO2013/037068 describes synthetic stool preparations comprising bacteria isolated from a fecal sample of a healthy donor and the use in treatment of diseases of the gastro intestinal system. The preparations described in that document are based on the combinations of bacteria strains isolated from a single donor, the combination being based on diversity and dominance in this donor. Although suitable in certain contexts, the proposed bacterial mix does not solve the question of compatibility of the used preparation with the receiving patient neither guarantees the maintenance of required functions throughout the application.

WO2012/142605 discloses compositions comprising preselected combinations of microorganisms, suitable in the treatment of intestinal disorders by rapid colonization. Although suitable, the compositions described are considered disadvantageous, as the strains are selected by relative abundance in a healthy population and do not show a rationale for rapid colonization. There is no function-based rationale behind the selection of strains, and no proposed method to guarantee the relative abundance of the single strains upon administration as well as no demonstration of the claim of being fast.

A number of publications relate to specific compositions of microbes and their use in the field of microbiome therapy. US2016/0243175 and WO2015/051323 disclose compositions comprising defined microbial consortia, suitable e.g. in the treatment of CDI, focusing exclusively on the inhibition of *C. difficile* through reduction of urease producing bacteria. WO2014/110685 discloses compositions comprising viable propionic acid-producing bacteria, suitable e.g. in the treatment of digestive diseases, such as infantile colics, through the utilization and elimination of produced lactate by propionic acid producing bacteria and hindrance of the utilization by other, potentially detrimental bacterial groups. US2016/0000838 discloses compositions comprising a single and specific *Faecalibacterium prausnitzii* strain, suitable e.g. in the treatment of inflammatory disorders, such as IBD without disclosing a mechanism of action. WO2016/086161 discloses compositions with increased abundance of commensal gut bacteria of the order Clostridiales, suitable in the treatment of GvHD (graft versus host disease). Both latter patents focus on replacing the under-represented bacteria through administration of viable bacteria or mixes thereof, without suggesting a rationale for in vivo viability and mechanisms of action.

Zihler et al. 2013 disclose a fermentation-based intestinal model for controlled ecological studies and propose a method to cultivate intestinal microbiomes in their totality starting from fecal material. Though stable in composition, the document is silent on the cultivation of a defined mix of strict anaerobic bacteria, i.e. a consortium, under the described continuous fermentation conditions.

In consequence, there is an unmet clinical need for treatment of diseases associated with intestinal microbiota dysbiosis, particularly recurrent CDI.

Thus, it is an object of the present invention to mitigate at least some of these drawbacks of the state of the art. In particular, it is an aim of the present invention to provide compositions suited for the treatment of diseases associated with intestinal microbiota dysbiosis.

These objectives are achieved by compositions as defined in claim 1, manufacturing methods as defined in claim 5 and pharmaceuticals as defined in claim 10. Further aspects of the invention are disclosed in the specification and independent claims, preferred embodiments are disclosed in the specification and the dependent claims.

It is particularly noted that the inventive compositions show similar or improved results when compared to the traditional FMT therapy in an acute DSS (dextran sulfate sodium) mouse model while avoiding its risks. It is further noted that the inventive compositions, comprising bacteria strains obtained by co-cultivation, show significantly improved results when compared to compositions comprising the same bacteria strains obtained by individual cultivation.

The present invention will be described in more detail below. It is understood that the various embodiments, preferences and ranges as provided/disclosed in this specification may be combined at will. Further, depending of the specific embodiment, selected definitions, embodiments or ranges may not apply.

Unless otherwise stated, the following definitions shall apply in this specification:

As used herein, the term "a", "an", "the" and similar terms used in the context of the present invention (especially in the context of the claims) are to be construed to cover both the singular and plural unless otherwise indicated herein or clearly contradicted by the context.

As used herein, the terms "including", "containing" and "comprising" are used herein in their open, non-limiting sense.

The term "Microbiota" is known and particularly denotes the totality of microbial life forms within a given habitat or host.

The term "Dysbiosis" is known and particularly denotes the alteration of the microbiota in comparison to the healthy state.

The term "Intermediate Metabolite" denotes the metabolites produced by members of the microbiota that are used as energy source by other members of the microbiota. Such intermediate metabolites are typically not enriched in the feces of a healthy individual.

The term "End Metabolites" denotes the metabolites produced by the intestinal microbiota that are not or only partially utilized by other members of the microbiota. End metabolites are partially absorbed by the host and partially secreted in the feces.

The term "Effluent" is known and particularly denotes the outflow of a continuous fermentation process containing consumed growth medium, bacteria and bacterial metabolites.

The terms "Bacteria" and "Bacteria Strain" are known and particularly denote the totality of the domain Bacteria. Due to its function, also the genera *Methanobrevibacter* and *Candidatus Methanomassiliicoccus* of the Domain Archaea shall be included in the term "Bacteria".

The present invention will be better understood by reference to the figures.

FIG. 1: Short chain fatty acid concentrations in a 200 ml bioreactor during establishment and stabilization of the bacterial consortium PB002 fermentation. The x-axis indicates the time in days starting at day 0 for inoculation of the bioreactor. The y-axis represents the concentration of metabolites in mM of acetate ( ), propionate ( ), butyrate ( ), formate ( ), lactate ( ) and succinate ( ).

Figure 2:
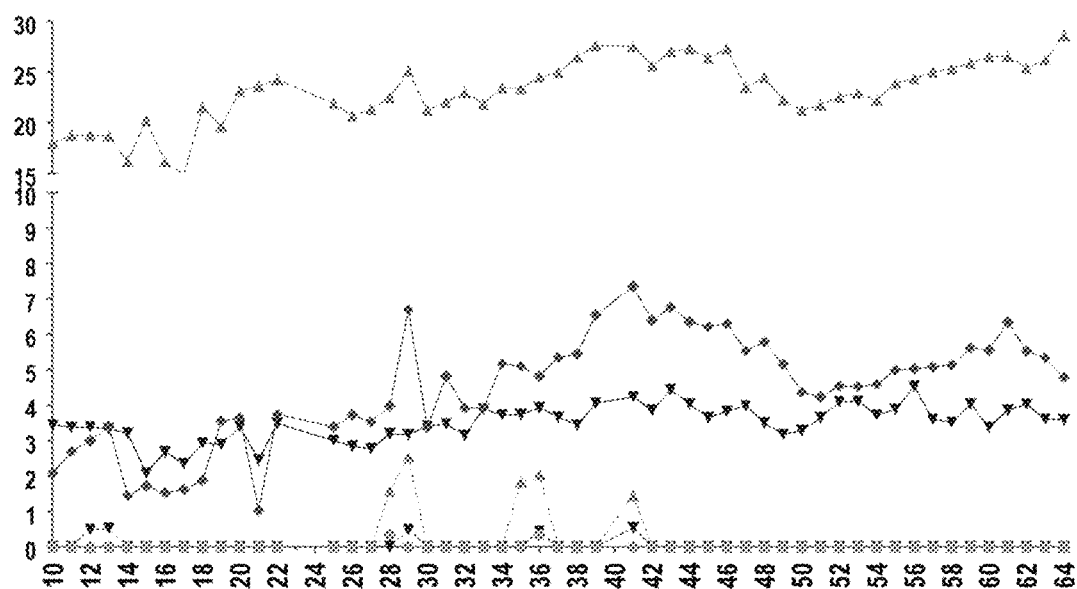

FIG. 2: Daily metabolite concentration of the continuously co-cultured bacterial consortium PB002 in a bioreactor. Day of sampling from day 10 to day 64 after inoculation are represented on the x-axis and the concentrations of acetate ( ), propionate ( ) butyrate ( ), formate ( ), lactate ( ), and succinate ( ) indicated in mM on the y-axis. Metabolites show to be stable over more than 50 days with no accumulation of the intermediate metabolites formate, lactate, or succinate.

Figure 3:
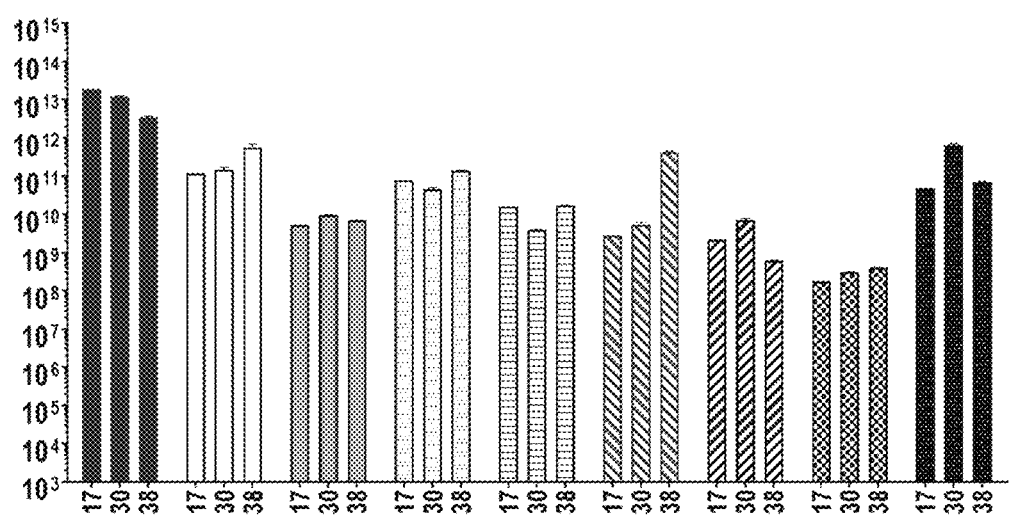

FIG. 3: Absolute abundances of all strains of the continuously cultured consortium PB002 at day 17, 30 and 38 after inoculation. Abundances were quantified using qPCR and are indicated in copies of the 16S rRNA gene/ml of culture for the strains representing A1 ( ), A2 ( ), A3 ( ), A4 ( ), A5 ( ) A6 ( ), A7 ( ), A8 ( ), and A9 ( ) Error bars represent standard deviations of technical replicates. qPCR quantification shows different abundances of the different functional groups and their stability throughout continuous fermentation.

Figure 4:
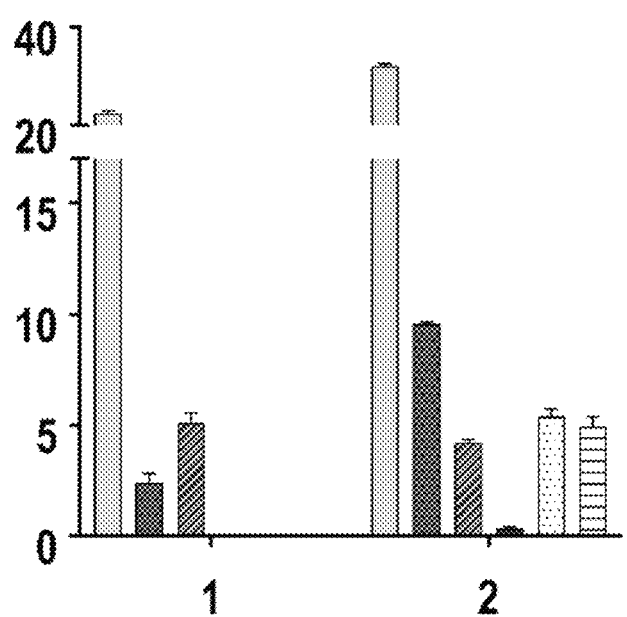

FIG. 4: Bacterial metabolite concentration in the bacterial suspensions used for transplantation. (1) was produced by continuous fermentation of PB002 and (2) was obtained by mixing of independent cultures of the 9 strains in PB002. Metabolites are represented in mM of acetate ( ), propionate ( ), butyrate ( ), succinate ( ), lactate ( ), formate ( ). The co-cultured suspension (1) shows no quantifiable intermediate metabolites as compared to the mix of pure cultures (2).

Figure 5:
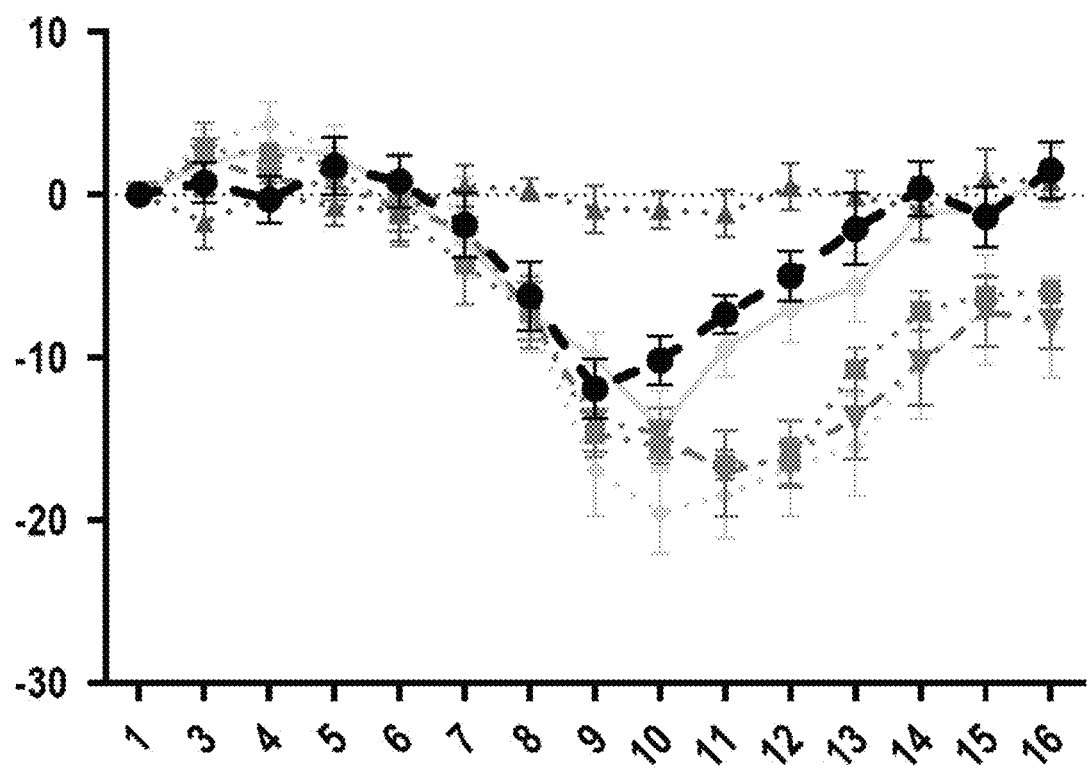

FIG. 5: Relative weight change of C57/B6 mice relative to their starting weight (indicated on the y-axis), over 15 days of experimentation, days are indicated on the x-axis. Mice were challenged with an acute DSS colitis adding 3% DSS in drinking water over 7 days (days 1-7) and subsequently given access to normal drinking water for the following 8 days for recovery (days 8-16). Groups represent: the control group that was not exposed to DSS ( ), the untreated DSS group ( ), the group treated with the inventive composition PB002 ( ), the group treated with the mix of independently cultured strains ( ), the group treated with the filtered supernatant of PB002 ( ) and the group treated with human fecal microbiome transplant ( ). Points are the means of all mice for each treatment group. Error bars indicate the SEM. Treatment group, receiving the inventive composition PB002, showed a weight recovery superior to all other treatment groups.

Figure 6:
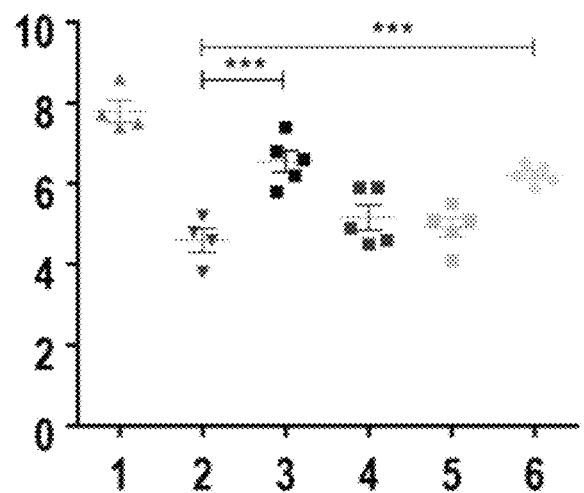

FIG. 6: Mouse colon length of individual C57/B6 mice at day 16 of experimentation indicated in cm on the y-axis. Groups represent the control group that was not exposed to DSS (1), the untreated DSS group (2), the group treated with the inventive composition PB002 (3), the group treated with the mix of independently cultured strains (4), the group treated with the filtered supernatant of PB002 (5) and the group treated with human fecal microbiome transplant (6). Each value represents a single mouse. Error bars indicate the SEM. Two way annova was performed. The inventive composition PB002 and FMT treatment showed highly significant increase of colon length with a p-value <0.001 as compared to the untreated DSS control (2).

Figure 7:
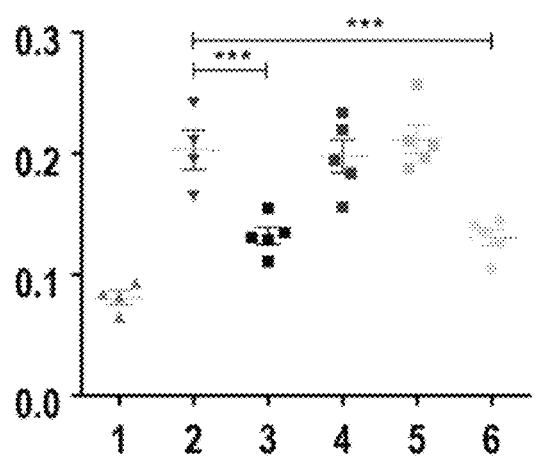

FIG. 7: Mouse spleen weight of individual C57/B6 mice at day 16 of experimentation indicated in g on the y-axis. Groups represent the control group that was not exposed to DSS (1), the untreated DSS group (2), the group treated with inventive composition PB002 (3), the group treated with the mix of independently cultured strains (4), the group treated with the filtered supernatant of PB002 (5) and the group treated with human fecal microbiome transplant (6). Each value represents a single mouse. Error bars indicate the SEM. Two way annova was performed. PB002 and FMT treatment showed highly significant decrease in spleen weight with a p-value <0.001 as compared to the untreated DSS control (2).

Figure 8:
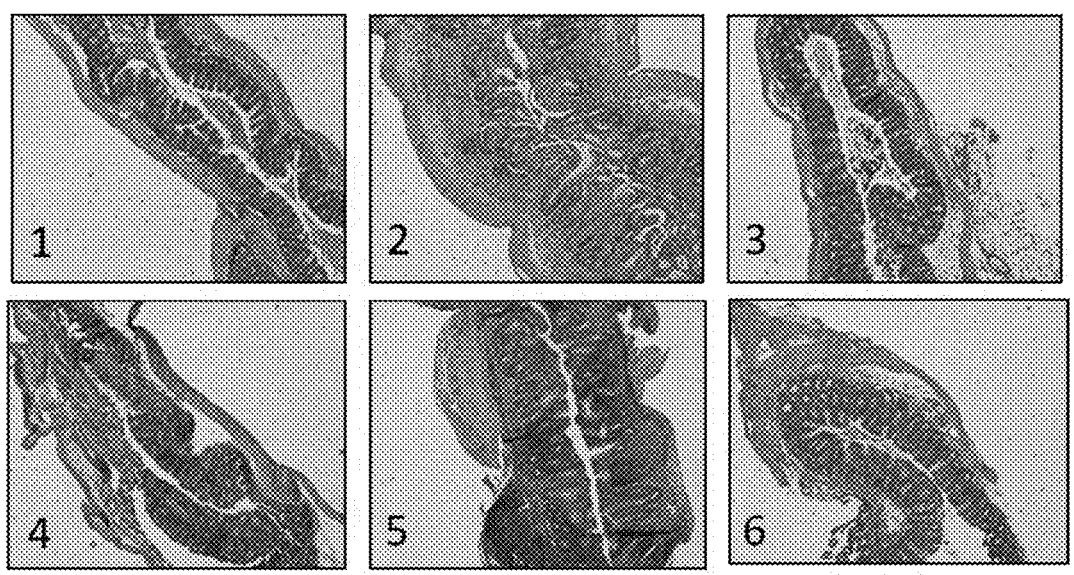

FIG. 8: Histological assessment of the epithelial inflammation of the cecum at day 16. Group that was not exposed to DSS (1), the untreated DSS group (2), the group treated with PB002 (3), the group treated with the mix of independently cultured strains (4), the group treated with the filtered supernatant of PB002 (5) and the group treated with human fecal microbiome transplant (6). Treatment groups (3) and (6) are the only treatment groups showing structural recovery of the epithelium comparable to the healthy control group (1) at the day of sacrifice as compared to (2), (4), and (5) that still display substantial degradation and inflammation of the epithelium in the cecum.

Figure 9:
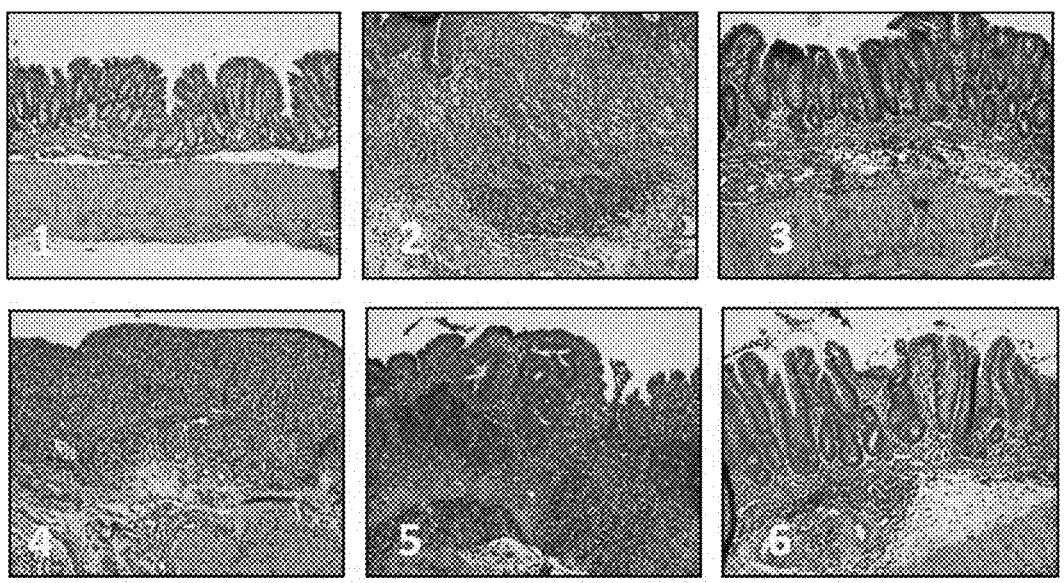

FIG. 9: Histological assessment of the epithelial inflammation of the lower intestine at day 16. Group that was not exposed to DSS (1), the untreated DSS group (2), the group treated with PB002 (3), the group treated with the mix of independently cultured strains (4), the group treated with the filtered supernatant of PB002 (5) and the group treated with human fecal microbiome transplant (6). Treatment groups (3) and (6) are the only treatment groups showing structural recovery of the epithelium comparable to the healthy control group (1) at the day of sacrifice as compared to (2), (4), and (5) that still display substantial degradation and inflammation of the epithelium in the lower intestine.

In more general terms, in a first aspect, the invention relates to new compositions, which are useful for example in the field of pharmacy. The inventive compositions comprise specific viable, live bacteria strains (i), intermediate metabolites to a maximum concentration, (ii) end metabolites (iii) to a specific minimum concentration and a dispersing medium (iv) as defined below. These compositions are obtainable as described below (second aspect) providing a stable, highly concentrated consortium of viable bacteria. These compositions are useful in pharmaceutical applications as described below (third aspect); due to the function-based selection of the bacteria strains in the compositions, a very low maximum amount of undesired intermediate metabolites (ii) and a very high amount of desired end metabolites (iii), representing physiologically relevant ratios, is ensured.

Fiber degradation by bacterial fermentation in the intestine is the central function of the intestinal microbiome (cf. Lacroix and Chassard (2013)). It is generally known that the metabolite concentrations obtained from fiber degradation are independent of the composition of the recipient's microbiome. It was surprisingly found that the effect of the inventive compositions is independent of the concentration of end metabolites and undesired intermediate metabolites in the gut of the recipient upon administration. Though present in most individuals, the single metabolic interactions are known to vary in their relative abundance between individuals. Bacteroidetes dominated microbiomes might enrich succinate while Ruminococcus enriched microbiomes might enrich formate upon degradation of fibers. The inventive compositions take into account the possible variations in different microbiome compositions in the patient population and re-balance dysbiosis independent of the nature thereof.

This aspect of the invention shall be explained in further detail below:

Component (i), Viable, Live Bacteria Strains:

The term viable, live bacteria strains is known in the field and particularly relates to bacteria strains (i) having a viability of over 50% (e.g. in pharmaceutical products), typically over 70% such as over 90% (e.g. products obtained according to the inventive process) as determined by flow cytometry. Viability over 90% is typically observed from the compositions as initially obtained by continuous cultivation, viability over 70% is typically observed after stabilization. As outlined in the experiments below (c.f. example 10), efficacy of the stabilized inventive compositions could be shown for bacteria strains having viabilities of at least 20%.

Bacteria strains useful in the context of this invention are described below as (A1) to (A9). The concentration of these bacteria strains (i) in the inventive compositions may vary over a broad range, typically the total concentration of all bacteria strains (A1) to (A9) is above $10^9$ bacteria per ml composition.

The inventive compositions comprise bacteria strains of groups (A1) to (A9) as defined herein. The presence of all 9 groups is important to ensure the beneficial pharmaceutical effects described below. Accordingly, groups (A1) to (A9) are present in the inventive compositions, further groups may be present as well, but are not required. Typically, bacteria strains of groups (A1) to (A9) are present; further groups of bacteria strains being absent.

As discussed below, groups (A1) to (A9) are defined by their functions. Such functions may be accomplished by one or more than one bacteria strain. Accordingly, each group comprises one or more, preferably one, bacteria strain.

In view of the intended use, bacteria strains (A1) to (A9) preferably belong to the group of intestinal bacteria strains.

As discussed below, the concentration of bacteria strains according to groups (A1) to (A9) may vary over a broad range. Typically, each group is present in a concentration below $10^{14}$ 16 S rRNA gene copies per ml composition. Typically, each group is present in a concentration above $10^5$ 16 S rRNA gene copies per ml composition, preferably above $10^6$ 16 S rRNA gene copies per ml composition, particularly preferably above $10^8$ 16 S rRNA gene copies per ml composition. The concentration of bacteria strains is quantified by qPCR, e.g. by using the primers listed in Table 1.

The bacteria strains are obtainable by co-cultivation, see $2^{nd}$ aspect. This co-cultivation ensures a balanced amount of each of the strains and the establishment of a metabolic interaction, thereby providing a synergistic interaction resulting in a higher amount of bacteria strains (A1) to (A9) and an increased robustness of the single strains and the mixes thereof.

Group (A1) comprises bacteria strains consuming sugars, fibers, and resistant starch, producing formate and acetate. Such bacteria strains are known and include bacteria of the genera *Ruminococcus, Dorea* and *Eubacterium* such as the species *Ruminococcus bromii* (ATCC 27255, ATCC 51896), *Ruminococcus lactaris* (ATCC 29176), *Ruminoccccus champanellensis* (DSM 18848, JCM 17042), *Ruminocccus callidus* (ATCC 27760), *Ruminococcus gnavus* (ATCC 29149, ATCC 35913, JCM 6515), *Ruminococcus obeum* (ATCC 29174, DSM 25238, JCM 31340), *Dorea longicatena* (DSM 13814, JCM 11232), *Dorea formicigenerans* (ATCC 27755, DSM 3992, JCM 31256), *Eubacterium eligens* (ATCC 27750, DSM 3376).

Group (A2) comprises bacteria strains consuming sugars, starch and acetate, producing formate and butyrate. Such bacteria strains are known and include bacteria of the genera *Faecalibacterium, Roseburia* and *Anaerostipes* such as the species *Faecalibacterium prausnitzii* (ATCC 27768, ATCC 27766, DSM 17677, JCM 31915), *Anaerostipes hadrus* (ATCC 29173, DSM 3319), *Roseburia intestinalis* (DSM 14610, CIP 107878, JCM 31262).

Group (A3) comprises bacteria strains consuming sugars and oxygen, producing lactate. Such bacteria strains are known and include bacteria of the genera *Lactobacillus, Streptococcus, Escherichia, Lactococcus, Enterococcus* such as the species *Lactobacillus rhamnosus* (ATCC 7469, DSM 20021, JCM 1136), *Streptococcus salivarius* (ATCC 7073, DSM 20560, JCM 5707), *Escherichia coli* (ATCC 11775, DSM 30083, JCM 1649), *Lactococcus lactis* (ATCC 19435, DSM 20481), *Enterococcus caccae* (ATCC BAA-1240, DSM 19114).

Group (A4) comprises bacteria strains consuming sugars, starch, and carbon dioxide, producing lactate, formate and acetate. Such bacteria strains are known and include bacteria of the genus *Bifidobacterium*, such as the species *Bifidobacterium adolescentis* (ATCC 15703, DSM 20083, JCM 1251), *Bifidobacterium angulatum* (ATCC 27535, DSM 20098), *Bifidobacterium bifidum* (ATCC 29521, DSM 20456, JCM 1255), *Bifidobacterium breve* (ATCC 1192, DSM 20213), *Bifidobacterium catenulatum* (ATCC 27539, DSM 16992, JCM 1194), *Bifidobacterium dentium* (ATCC 27534, DSM 20436, JCM 1195), *Bifidobacterium gallicum* (ATCC 49850, DSM 20093, JCM 8224), *Bifidobacterium longum* (ATCC 15707, DSM 20219, JCM 1217), *Bifidobacterium pseudocatenumlatum* (ATCC 27919, DSM 20438, JCM 1200).

Group (A5) comprises bacteria strains consuming lactate and proteins, producing propionate and acetate. Such bacteria strains are known and include bacteria of the genera

*Clostridium, Propionibacterium, Veillonella, Megasphaera* such as the species *Clostridium aminovalericum* (ATCC 13725, DSM 1283, JCM 1421), *Clostridium celatum* (ATCC 27791, DSM 1785, JCM 1394), *Clostridium lactatifermentans* (DSM 14214), *Clostridium neopropionicum* (DSM 3847), *Clostridium propionicum* (ATCC 25522, DSM 1682, JCM 1430), *Megasphaera elsdenii* (ATCC 25940, DSM 20460, JCM 1772), *Veillonella montpellierensis* (DSM 17217), *Veillonella ratti* (ATCC 17746, DSM 20736, JCM 6512).

Group (A6) comprises bacteria strains consuming lactate and starch, producing acetate, butyrate and hydrogen. Such bacteria strains are known and include bacteria of the genera *Anaerostipes, Clostridium* and *Eubacterium* such as the species *Anaerostipes caccae* (DSM 14662, JCM 13470), *Clostridium indolis* (ATCC 25771, DSM 755, JCM 1380), *Eubacterium hallii* (ATCC 27751, DSM 3353, JCM 31263), *Eubacterium limosum* (ATCC 8486, DSM 20543, JCM 6421), *Eubacterium ramulus* (ATCC 29099, DSM 15684, JCM 31355).

Group (A7) comprises bacteria strains consuming sugar, starch and formate, producing lactate, formate and acetate. Such bacteria strains are known and include bacteria of the genus *Collinsella*, such as the species *Collinsella aerofaciens* (ATCC 25986, DSM 3979, JCM 10188), *Collinsella intestinalis* (DSM 13280, JCM 10643), *Collinsella stercoris* (DSM 13279, JCM 10641).

Group (A8) comprises bacteria strains consuming succinate, producing propionate and acetate. Such bacteria strains are known and include bacteria of the genera *Phascolarctobacterium, Dialister* such as the species *Phascolarctobacterium faecium* (DSM 14760), *Dialister succinatiphilus* (DSM 21274, JCM 15077), *Dialister propionifaciens* (JCM 17568).

Group (A9) comprises bacteria strains consuming sugars, fibers, formate and hydrogen, producing acetate and butyrate. Such bacteria strains are known and include bacteria of the genus *Blautia* and archaea of the genera *Methanobrevibacter, Methanomassiliicoccus* such as the species *Blautia hydrogenotrophica* (DSM 10507, JCM 14656), *Blautia producta* (ATCC 27340, DSM 2950, JCM 1471), *Methanobrevibacter smithii* (ATCC 35061, DSM 861, JCM 328), *Candidatus Methanomassiliicoccus* intestinalis.

Such bacteria strains further include bacteria of the genera *Acetobacterium, Clostridium, Moorella* and *Sporomusa*, such as the species *Acetobacterium carbinolicum* (ATCC BAA-990, DSM 2925), *Acetobacterium malicum* (DSM 4132), *Acetobacterium wieringae* (ATCC 43740, DSM 1911, JCM 2380), *Clostridium aceticum* (ATCC 35044, DSM 1496, JCM 15732), *Clostridium glycolicum* (ATCC 14880, DSM 1288, JCM 1401), *Clostridium magnum* (ATCC 49199, DSM 2767), *Clostridium mayombei* (ATCC 51428, DSM 2767).

The bacteria strains as defined herein are in each case identified through classification of the full 16S rRNA gene with assignment for the different taxonomic levels Phylum: 75%, Class: 78.5%, Order: 82%, Family: 86.5%, Genus: 94.5%, Species: 98.65% of sequence similarity. Such assignment may be achieved by using SILVA Software (SSURef NR99 128 SILVA) and using the HITdb (Ritari et al., 2015).

In pure culture, the functions of single bacteria strains (A1) to (A9) may be bidirectional. For example, (A7) may either produce or consume formate. However, when combined in the inventive compositions, the bacteria strains show the properties discussed herein, consuming intermediate metabolites (succinate, lactate, formate) and producing end metabolites exclusively (acetate, propionate, butyrate).

Component (i) may be described as a synthetic and symbiotic consortium which is characterized by a combination of microbial activities forming a trophic chain from complex fiber metabolism to the canonical final SCFA (Short chain fatty acids) found in the healthy intestine: acetate, propionate and butyrate exclusively. The trophic completeness of component (i) prevents the accumulation of potentially toxic or pain inducing products such as $H_2$, lactate, formate and succinate. Activities are screened by functional characterization on different substrates of the human gut microbiota. However, type and origin of strains can be selected according to the targeted level of complexity of the synthetic and symbiotic consortia in order to recompose a complex microbiota replacing fecal transplants. The different bacteria strains (A1) to (A9) grow as a consortium, ensuring degradation of complex polysaccharides usually found in the gut (resistant starch, xylan, arabinoxylan and pectin), reutilization of sugars released, removal of $O_2$ traces for maintenance of anaerobiosis essential for growth, production of key intermediate metabolites (acetate, lactate, formate, CO2 and H2), reutilization of all intermediate metabolites and production of end metabolites found in a healthy gut (acetate, propionate and butyrate). The microbial symbiotic consortia exclusively produce end-fermentation products that are beneficial and used by the host for different functions such as acetate (energy source for heart and brain cells), propionate (metabolized by the liver) and butyrate (the main source of energy for intestinal epithelial cells).

The combination of strains A1 to A9 is chosen to:
Degrade the main energy sources in the gut including fibers and intermediate metabolites (all groups);
Protect anaerobiosis by reduction of the eventual $O_2$ through respiration (group A3);
Produce the main end metabolites found in the intestine (A1, A2, A3, A4, A5, A9);
Prevent the enrichment of intermediate metabolites (A5, A6, A7, A8, A9).

The combination of strains from the functional groups (A1) to (A9) encompass the key functions of fiber degradation by the microbiome as described by Lacroix and Chassard in 2013 and results, if cultured together, in a trophic chain analog to the healthy intestinal microbiome in its capacity to exclusively produce end metabolites from complex carbohydrates without accumulation of intermediate metabolites.

It is particularly beneficial that the combination of strains from the functional groups (A1) to (A9) prevents the enrichment of intermediate metabolites independent of the composition of the recipient's microbiome and the relative concentration of the enriched intermediate metabolites.

Component (ii), Intermediate Metabolites:

The inventive compositions comprise intermediate metabolites in very low concentrations. The low concentration of intermediate metabolites is important to achieve the pharmaceutical beneficial effects discussed below. It is important to note these low concentrations of intermediate metabolites in the context of high concentrations of end metabolites.

Advantageously, the amount of succinate is below 5 mM, preferably below 2 mM, much preferably below 1 mM.

Advantageously, the amount of formate is below 5 mM, preferably below 2 mM, much preferably below 1 mM.

Advantageously, the amount of lactate is below 5 mM, preferably below 2 mM, much preferably below 1 mM.

The concentration may be determined using HPLC-RI. This method has a detection limit of about 1 mM. A reference to below 1 mM thus also refers to a concentration below detection limit.

Component (iii), End Metabolites:

The inventive compositions comprise end metabolites in high concentrations. The high concentration of end metabolites is important to achieve the pharmaceutical beneficial effects discussed below. It is important to note these high concentrations of end metabolites in the context of low concentrations of intermediate metabolites.

Advantageously, the amount of acetate is above 10 mM, preferably above 30 mM, much preferably above 50 mM. Advantageously, the amount of acetate is below 120 mM.

Advantageously, the amount of propionate is above 2 mM, preferably above 5 mM, much preferably above 10 mM. Advantageously, the amount of propionate is below 60 mM.

Advantageously, the amount of butyrate is above 2 mM, preferably above 5 mM, much preferably above 10 mM. Advantageously, the amount of butyrate is below 60 mM.

The concentration may be determined using the same methods as discussed above for intermediate metabolites.

Component (iv), Dispersing Medium:

The inventive compositions comprise a dispersing medium (iv). Such medium (iv) is added for a variety of reasons. First, the dispersing medium particularly ensures that bacteria (i) remain as viable live bacteria. Further, the dispersing medium guarantees growth of all groups (A1)-(A9) in the desired ratios. Still further, the dispersing medium plays an important role in recovery of the bacteria strains after storage. A broad range of solid or liquid dispersing media are known and may be used in the context of the present invention.

Suitable media (iv) include liquid media and solid supports. Liquid media generally comprise water and may thus also be termed aqueous media. Such liquid media may comprise a culture medium, a cryoprotective medium and/or a gel forming medium. Solid media may comprise a polymeric support.

Cryoprotecting media are known in the field and include liquid compositions that allow freezing of bacteria strains essentially maintaining their viability. Suitable cryoprotecting agents may be identified by the skilled person, glycerol may be named by way of example. Inventive compositions comprising cryoprotecting agent are typically present as a suspension. Suitable amounts of cryoprotecting media may be determined by the skilled person in routine experiments; suitable are 5-50%, preferably 10-40%, such as 30%.

Culture media are known in the field and include liquid compositions that allow the growth of bacterial strains. Typically, culture media include a carbon source (glucose, galactose, maltose), "fibers" (preferably pectine, arabinogalactan, beta-glucan, starch, fructo-oligosacharides, galacto-oligosacharidesand, xylan, arabinoxylans, cellulose), proteins (preferably yeast extract, casein, skimmed milk), co-factors (short chain fatty acids, hemin), vitamins (preferably biotin, cobalamin (B12), 4-aminobenzoic acid, folic acid, pyridoxamine hydrochloride) and reducing agents (preferably cysteine, titianium(III)-citrate, yeast extract, sodium thioglycolate, dithiotreitol, sodium sulphide, hydrogen sulphite, ascorbate). Inventive compositions comprising culture media are typically present as a suspension.

Gel forming media are known in the field and include compositions comprising a gelling agent. Suitable gelling agents include polymers such as agar, alginate, carrageenan, cellulose and its derivatives, collagen, gelatin, epoxy resin, photo cross-linkable resins, polyacrylamide, polyester, polystyrene and polyurethane, polyacrylamide gel, alginate gel, k-carrageenan, photo-cross-linkable resins, xanthan or gellan.

In a second aspect, the invention relates to a method for manufacturing compositions as defined herein, said method comprising the step of co-cultivating bacteria strains (A1) to (A9). This manufacturing method ensures the presence of viable bacteria strains (A1) to (A9) in suitable concentrations, and simultaneously the low concentration of intermediate metabolites, as well as the high concentration of end metabolites in the inventive compositions. Further, this method allows manufacturing compositions comprising a defined mix of bacteria strains (A1) to (A9).

The step of co-cultivation, denoted as step (b) herein, is typically complemented by a preceding step (a), providing the bacteria strains (A1) to (A9). Further, step (b) may be complemented by post-treatments, as defined in step (c). Thus, the inventive method advantageously comprises the steps of: (a) providing compositions comprising viable live bacteria strains (A1) to (A9) as defined herein; (b) co-cultivating the compositions of step (a); and optionally (c) post treatment steps.

This aspect of the invention shall be explained in further detail below:

Providing Individual Bacteria Strains, Step (a):

providing a consortium of bacteria strains to a co-cultivation step is known per se and may be applied to the individual strains (A1) to (A9) in a known manner.

Advantageously, step (a) comprises two individual steps (a1) and (a2). First, bacteria strains (A1) to (A9) are provided and separately cultivated. Second, the materials obtained in (a1) are combined and co-cultivated until intermediate metabolites succinate, formate and lactate are each below 5 mM (a2).

Advantageously, step (a1) is performed batchwise.

Advantageously, cultivation of step (a1) is performed in the presence of a substrate specific for each of said bacteria strains (A1) to (A9).

Advantageously, intestinal bacteria strains previously isolated and characterized from one or more healthy donors are used in this step (a1).

Advantageously, step (a2) is performed batchwise. Advantageously, cultivation of step (a2) is performed in the presence of amicase, yeast extract, arabinogalactan, fructo-oligosaccharides, soluble starch, resistant starch, xylan; typically at a pH 5.5-6.5 and under oxygen-free atmosphere.

Advantageously, step (a2) is terminated, once intermediate metabolites succinate, formate and lactate are each below 5 mM, preferably each below 2 mM, much preferred each below 1 mM.

Co-Cultivation of Bacteria Strains, Step (b):

As discussed herein, the co-cultivation of step (b) is considered a key element for successful manufacturing the inventive compositions and to obtain the pharmaceutical results described. It is apparent that step (b) follows step (a2).

Such co-cultivation may be performed according to known principles, commercially available equipment (such as a bioreactor) and considering the bacteria strains to be cultivated.

Suitable culture media thus comprise amicase, yeast extract, arabinogalactan, fructo-oligosaccharides, soluble starch, resistant starch, xylan and co-factors or vitamins as described above.

Co-cultivation is typically performed at a pH 5.5-7, preferably at pH 6.5.

Co-cultivation is typically performed under an oxygen free atmosphere, such as CO2 or nitrogen, preferably CO2.

Co-cultivation is typically performed at constant temperature, typically 37° C. Advantageously, co-cultivation is performed continuously typically at a flow rate of 12.5-25 ml/h, preferably at 12.5 ml/h. Accordingly, the co-cultivation of step (b) may be performed in a bioreactor using continuous fermentation and the conditions described herein.

The co-cultivation as described herein provides bacteria consortia in a specific balanced, symbiotic composition, thereby providing for a synergistic effect.

Post-Treatment, Step (c):

Post treatment of bacteria consortia, e.g. as obtained from a bioreactor, is known to the skilled person. The material obtained in step (b) is typically present in the form of a suspension, said suspension comprising components (i), (ii) and (iii) as defined herein, dispersed in an aqueous medium that may contain further components, such as non-used substrates, pH modifiers and/or cryoprotectants. This initially obtained product may be directly used in the pharmaceutical applications as described herein ($3^{rd}$ aspect), which is considered a significant advantage of the inventive method. Alternatively, the initially obtained product may be subjected to post-treatment steps, such as those described herein. Such post-treatment particularly aims in improving product quality, storage stability, and/or alternative pharmaceutical formulations.

In one embodiment, step (c) comprises stabilization of the product by adding a cryoprotectant. Thus, the invention also relates to a manufacturing method as described herein wherein in step (c) the mixture of strains comprising (A1) to (A9) is combined with a cryoprotectant.

As the experimental results show, c.f. FIG. 5, bacteria consortia (A1) to (A9) have different properties, depending on either their co-cultivation or their separate cultivation. This finding proves that the compositions comprising such bacteria consortia differ. As a consequence, the invention also relates to compositions comprising components (i), (ii) and (iii) (particularly: (i)-(iv)) as defined herein, characterized in that said bacteria strains (A1) to (A9) (i.e. component (i)) are obtained by co-cultivation; preferably by co-cultivation at pH 5.5-6.5 under inert (particularly: oxygen-free) atmosphere, and particularly preferably obtained according to steps (a1), (a2) and (b) as described herein.

In summary, this aspect describes the production of new consortia based on their trophic interaction and their capacity to combine key functions of the intestinal ecosystem, particularly for replacing FMT as therapeutics. For this strategy, the assembly of microbial consortia is not based on the phylogenic distribution of the microbes in healthy intestinal microbiota, but relying on the functionality of key microbial groups. Thereby, the mode of action of successful FMT but with a reduced set of bacteria is guaranteed. The presented consortia are designed on a function-based rationale in order to restore or re-balance the lacking or dysbalanced functions in dysbalanced intestinal microbiomes, i.e. dysbiosis.

In a third aspect, the invention relates to the use of compositions as described herein as pharmaceuticals.

This aspect of the invention shall be explained in further detail below:

The compositions as described herein have pharmaceutical applications. Thus, the invention provides for the compositions as described herein which are pharmaceutical compositions comprising components (i) to (iv) as disclosed herein.

Specifically, the invention provides for compositions comprising co-cultivated viable, live, human, intestinal bacteria strains (A1) to (A9) as defined in the first aspect of the invention, for use as a pharmaceutical.

In an advantageous embodiment, the pharmaceutical compositions are free of, or essentially free of other viable, live bacteria strains.

In a further advantageous embodiment, the pharmaceutical compositions are free of, or essentially free of intermediate metabolites (succinate, formate and lactate).

In a further advantageous embodiment, the pharmaceutical compositions further comprise a culture medium, preferably a culture medium as disclosed in the second aspect of the invention.

Such pharmaceutical compositions may be formulated according to known principles and adapted to various modes of administration. In one embodiment, the inventive pharmaceutical compositions are adapted to rectal administration. In one further embodiment, the inventive pharmaceutical compositions are adapted to oral administration.

The pharmaceutical compositions may find use in a number of indications. Thus, the invention provides for pharmaceutical compositions as described herein for use in the prophylaxis, treatment, prevention or delay of progression of a disease associated with intestinal microbiome dysbalance or associated with microbiota dysbiosis. It is generally accepted that dysbiosis originates from an ecological dysbalance (e.g. based on trophism), characterized by disproportionate amounts or absence of bacteria strains belonging to single functional groups within the microbiome of the patient which are essential for the establishment and/or maintenance of a healthy microbiome.

Advantageously, such a disease is selected from intestinal infections, including *Clostridium difficile* infection (CDI), vancomycin resistant enterococci (VRE), post-infectious diarrhea, inflammatory bowel diseases (IBD), including ulcerative colitis (UC) and Crohn's disease (CD).

The inventive pharmaceutical compositions are particularly suited for treatment of IBD and CDI. Increasing prevalence of recurrent CDI, and IBD is a worldwide major concern. The lack of efficient therapies has given rise to an ancient medical practice, FMT (which denotes the use of a fresh or frozen suspension of fecal material as therapeutic, through transfer into the colon through the oral or anal route). FMT is the only effective treatment in last resort cases of recurrent CDI, with a striking efficacy over 90% and fast recovery of bowel function. However, FMT represents a significant risk for the patient, including disease transmission, lack of compatibility between recipient and donor, lack of control over mode of action. Therefore, FMT is currently only tolerated for untreatable CDI. Its efficiency based on a functional restitution of the microbiome is however undisputed.

The inventive pharmaceutical compositions now address the disadvantages of FMT. The compositions provide consortia of bacteria for replacing FMT by defined and effective therapeutics. The inventive approach replaces the multitude of intestinal bacteria (>500 species per individual) according to FMT by a defined, minimal and recipient-independent set of bacteria strains. The formulation of consortia is based on key bacteria with complementary functionality in order to grow on fiber and proteinous substrates only. Functionality is designed to cover the required metabolic pathways essential for the functioning of a complex intestinal microbiota and prevention of enrichment of intermediate metabolites, thereby generating the canonical, healthy fingerprint of a microbiota including acetate, propionate and butyrate only. The formulation of these reduced consortia using a defined number of bacteria strains is designed to establish conditions promoting a balanced and directed growth of the different functional groups of bacteria strains lost or dysbalanced in the patient's microbiota. This will be achieved by the re-establishment of the ecological niches and metabolic gradients required for the optimal growth of the missing or under-represented intestinal bacteria. The consortium guarantees the exclusive production of essential end metabolites and the elimination of enriched and/or inhibitory intermediate metabolites both major reasons causing an ecological dysbalance. The inventive compositions comprising microbial consortia defined by their functionality (A1) to (A9) represent the most robust, effective, stable and fully characterized microbial community, developed as alternative to known FMT strategies. Without being bound to theory, it is believed that functional restorations of the microbial activities are ensured by trophically interacting microbial consortia formulated for reproducing optimal microbial activities and intestinal tropism.

The surprising good results obtained with the inventive compositions are shown in FIG. 5. It is particularly referred to the superiority of the inventive composition ( ) in relation to the response time as compared to the currently used FMT ( ) It is further surprising that the conditioning through co-cultures results in a fast and robust reversal of colitis symptoms as compared to the mixing of single cultures ( ), a method often suggested for the production of consortia.

This invention also provides for pharmaceutical compositions adapted for personalized medicine, thereby targeting diseases with associated microbiota dysbiosis to specific patient groups or individuals. Bacteria showing similar functionalities but different taxonomic identities can be replaced and exchanged in component (i) used for treatment according to the loss of bacteria detected in patients or specific indications. Loss in diversity and functionality can be targeted for the first time, since the consortium approach allows the controlled re-establishment of single niches in the patient's gut. For example, the engraftment of a formate producing *Bifidobacterium* will be guaranteed by the combination with the formate utilizing *Blautia* strain in order to avoid enrichment of the intermediate metabolite, that would lead to the elimination of both strains.

To further illustrate the invention, the following examples are provided. These examples are provided with no intend to limit the scope of the invention.

EXAMPLE 1: RATIONALE, FUNCTIONAL GROUPS

Bacterial strains were isolated from healthy donors using Hungate anaerobic culturing techniques (Bryant, 1972) and characterized for growth and metabolite production on M2GSC Medium (ATCC Medium 2857) and modifications thereof whereby the carbon sources glucose, cellobiose and starch were replaced by specific substrates including intermediate metabolites and fibers found in the human intestine. Metabolites produced were quantified using HPLC-RI. The concentrations of the metabolites were quantified by refractive index detection HPLC (Thermo Scientific Accela™, ThermoFisher Scientific) analysis was performed using a SecurityGuard Cartridges Carbo-H (4×3.0 mm) (Phenomenex, Torrence, USA) as guard-column connected to a Rezex ROA-Organic Acid H+ column (300×7.8 mm) (Phenomenex). Bacterial cultures to be analyzed were centrifuged at 14.000-xg for 10 min at 4° C. Filter-sterilized (0.45 µL) supernatants were analyzed. Injection volume for each sample was 40 µL. HPLC was run at 40° C. with a flow rate of 0.4 mL/min and using $H_2SO_4$ (10 mM) as eluent. Peaks were analyzed using AgilentEzChrome Elite software (Version: 3.3.2 SP2, Agilent Technologies, Inc. Pleasanton, USA). Clusters were formed based on substrate usage and metabolite production. Functional groups were defined as combinations of substrate-utilization and metabolite-production as described in claim 1. 9 strains were selected within those clusters in order to assemble the core intestinal carbohydrate metabolism and result in an exclusive production of end metabolites, i.e. acetate, propionate and butyrate, without accumulation of intermediate metabolites, i.e. formate, succinate, lactate.

As outlined above, the combination of 9 strains is chosen to:

Degrade the main energy sources in the gut including fibers and intermediate metabolites (all groups)

Protect anaerobiosis by reduction of the eventual $O_2$ through respiration (group A3)

Produce the main end metabolites found in the intestine (A1, A2, A3, A4, A5, A9)

Prevent the enrichment of intermediate metabolites (A5, A6, A7, A8, A9) independent of the composition of the recipient's microbiome.

For group (A1), *Ruminococcus bromii* was cultivated in YCFA medium (Duncan, Hold, Harmsen, Stewart, & Flint, 2002) for 48 hours using the Hungate technique (Bryant, 1972) resulting in the production of formate (>15 mM) and acetate (>10 mM) as quantified by HPLC-RI.

For group (A2), *Faecalibacterium prausnitzii* was cultivated in M2GSC medium (ATCC Medium 2857) for 48 hours using the Hungate technique (Bryant, 1972) resulting in the consumption of acetate (>10 mM) and in the production of formate (>20 mM) and butyrate (>15 mM) as quantified by HPLC-RI.

For group (A3), *Lactobacillus rhamnosus* was cultivated in MRS Broth (Oxoid) for 48 hours using the Hungate technique resulting in the production of lactate (>50 mM) and formate (>10 mM) as quanitified by HPLC-RI.

For group (A4), *Bifidobacterium adolescentis* was cultivated in YCFA medium (Duncan et al., 2002) for 48 hours using the Hungate technique (Bryant, 1972) resulting in the production of acetate (>50 mM), formate (>15 mM) and lactate (>5 mM) as quantified by HPLC.

For group (A5), *Clostridium lactatifermentans* was cultivated in modified M2-based medium (ATCC Medium 2857) supplemented with DL-lactate [60 mM] instead of a carbohydrate source for 48 hours using the Hungate technique resulting in the consumption of lactate (at least 30 mM) and in the production of propionate (>30 mM), acetate (>10 mM) as detected by HPLC-RI.

For group (A6), *Eubacterium limosum* was cultivated in YCFA medium (Duncan et al., 2002) for 48 hours using the Hungate technique (Bryant, 1972) resulting in the production of acetate (>10 mM) and butyrate (>5 mM) as quantified by HPLC-RI.

For group (A7), *Collinsella aerofaciens* was cultivated in YCFA medium (Duncan et al., 2002) for 48 hours using the Hungate technique resulting in the production of formate (+23.71 mM), lactate (+19.18 mM) and acetate (+16.33 mM) as quantified by HPLC-RI.

For group (A8), *Phascolarctobacterium faecium* was cultivated in M2-based medium (ATCC Medium 2857) supplemented with succinate (60 mM) as sole carbohydrate source for 48 hours using the Hungate technique (Bryant, 1972) resulting in the full consumption of succinate (60 mM) and in the production of propionate (60 mM) as quantified by HPLC-RI.

For group (A9), *Blautia hydrogenotrophica* was cultivated in anaerobic AC21 medium (Leclerc, Bernalier, Donadille, & Lelait, 1997) for >75 hours using the Balch type tubes resulting in the production of acetate (>20 mM) as quantified by HPLC-RI, and consumption of hydrogen.

The combination of strains from the functional groups (A1)-(A9) encompass key functions of the microbiome and results, if cultured together, in a trophic chain analog to the healthy intestinal microbiome in its capacity to exclusively produce end metabolites from complex carbohydrates without accumulation of intermediate metabolites.

EXAMPLE 2: ASSEMBLY OF CONSORTIUM

In order to establish the 9 strains forth on named PB002 in a growing and metabolically interacting manner, a previously validated model for anaerobic intestinal fermentations (Zihler et al., 2013) was adapted using a simplified medium based on YCFA (DSMZ Media No 1611). Thereby, the 5 g of glucose that are the carbon source in YCFA were replaced by 2 g/L of pectin (Sigma Aldrich), 1 g/L of fructo-oligosacharaides (FB97, Cosucra), 3 g/L of potato starch (Sigma Aldrich), and 2 g/L of corn starch (Sigma Aldrich). A 200 ml bioreactor (Infors HT) was inoculated with a mix of overnight cultures of all 9 strains and inoculated anaerobically at a 1/100 dilution. The bioreactor was consecutively operated at pH 6.5 for 24 h in order to allow growth of primary degraders and sub sequential consumption of the produced intermediate metabolites. Growth was monitored by base consumption, and optical density of the bioreactor. Metabolites were monitored using HPLC-RI as described above. The evolution of metabolite production of the bioreactor during the establishment of PB002 is plotted in FIG. 1. After the first batch-fermentation, new medium was fed by removing half of total volume and refilling with medium to the original volume of 200 ml in the bioreactor. After two 24-hour batch fermentations the metabolic profile did not contain any intermediate metabolites and more than 40 mM acetate and over 5 mM of propionate and butyrate each. From the end of the second batch fermentation on, the bioreactor was operated continuously at a volume of 200 ml, a flow rate of 12.5 ml/h and a pH of 6.5. Subsequently, a stable metabolic profile established within 7 days after inoculation containing exclusively the desired end metabolites of acetate, propionate and butyrate without detection of intermediate metabolites showing constant production of all desired metabolites without washout of any functional group. PB002 could therefore be cultured in a bioreactor and showed the desired properties of the intestinal microbiome, i.e. degradation of fibers and proteins into exclusively end-metabolites, a clear indication that the desired interactions and metabolic activities described in example 1 were established in a continuously operated bioreactor.

EXAMPLE 3: STABILITY OF CONSORTIUM

In order to test the robustness and aptitude for continuous production of PB002, the bioreactor established in example 2 was further continuously operated at an operating volume of 200 ml, under agitation at 120 rpm, controlled pH of 6.5, constant flushing with CO2 and continuous feeding at 12.5 ml/h with the medium, described in example 2. Metabolite composition in the bioreactor was measured daily using HPLC-RI (FIG. 2). PB002 was maintained stable for more 60 days after inoculation with a metabolic profile consisting of exclusively acetate, propionate and butyrate, indicating the maintenance of the PB002 consortium over time and the robustness of interactions as well as the completeness of the trophic chain.

EXAMPLE 4: REL. QUANTIFICATION OF CONSORTIUM

To test maintenance of all 9 members of PB002 in the bio-reactor over time qPCR quantification of the single strains of the consortium was performed on days 17, 30, and 38 of the fermentation using the primers listed in table 1.

TABLE 1

| Group *) | Bacteria strains | Primer FW 5'-3' | Primer RV 5'-3' |
|---|---|---|---|
| A1 [1)] | *Ruminococcus bromii* | CGCGT GAAGG ATGAA GGTTT TC (SEQ ID NO. 1) | TCAGT TAAAG CCCAG CAGGC (SEQ ID NO. 2) |
| A2 [1)] | *Faecalibacterium prausnitzii* | CGCGG TAAAA CGTAG GTCAC A (SEQ ID NO. 3) | CTGGG ACGTT GTTTC TGAGT TT (SEQ ID NO. 4) |
| A3 [1)] | *Lactobacillus rhamnosus* | GGAAT CTTCC ACAAT GGACG CA (SEQ ID NO. 5) | CATGG AGTTC CACTG TCCTC TT (SEQ ID NO. 6) |
| A4 [1)] | *Bifidobacterium adolescentis* | GGAAT CTTCC ACAAT GGACG CA (SEQ ID NO. 7) | ACCAC CTGTG AACCC GC (SEQ ID NO. 8) |
| A5 [1)] | *Clostridium lactatifermentans* | GCACT CCACC TGGGG AGT (SEQ ID NO. 9) | CAACC TTCCT CCGGG TTATC CA (SEQ ID NO. 10) |
| A6 [2)] | *Eubacterium limosum* | GGCTT GCTGG ACAAA TACTG (SEQ ID NO. 11) | CTAGG CTCGT CAGAA GGATG (SEQ ID NO. 12) |

TABLE 1-continued

| Group *) | Bacteria strains | Primer FW 5'-3' | Primer RV 5'-3' |
|---|---|---|---|
| A7 [1] | Collinsella aerofaciens | GGTAG GGGAG GGTGG AAC (SEQ ID NO. 13) | GCGGT CCCGC GTGGG TT (SEQ ID NO. 14) |
| A8 [1] | Phascolarcto-bacterium faecium | GGAGT GCTAA TACCG GATGT GA (SEQ ID NO. 15) | CCGTG GCTTC CTCGT TTACT (SEQ ID NO. 16) |
| A9 [1] | Blautia hydrogenotrophica | CGTGA AGGAA GAAGT ATCTC GGTA (SEQ ID NO. 17) | TCAGT TACCG TCCAG CAGGC C (SEQ ID NO. 18) |
| A1-A9 [3] | All bacteria | GTGST GCAYG GYTGT CGTCA (SEQ ID NO. 19) | ACGTC RTCCC CRCCT TCCTC (SEQ ID NO. 20) |

*) sources: (1) DECIPHER database; (2) Wang et al. (1996), (3) Maeda et al., (2003)

DNA from pellets of the fermentation effluent was extracted using the FastDNA™ SPIN Kit for Soil (MP Bio). Genomic DNA extracts were 50-fold diluted using DNA-free $H_2O$. qPCRs were performed using Mastermix SYBR® green 2× and LowRox (Kapa Biosystems), primers (10 µM) and DNA-free $H_2O$ were used in a ABI 7500 FAST thermal cycler (Applied Biosystems) as recommended by the producer and quantified using standards of amplified whole 16S rRNA gene amplicon sequences of the strains used for the consortium cloned into the pGEMT easy vector (Promega, Madison Wis., USA). Amplification of the whole 16S rRNA gene was performed with a combination of whole 16S rRNA gene amplification primers using one forward and one reverse primer of from the primers listed in Table 2. qPCR quantification of the single strains is shown in copies of genomic 16S rRNA gene per ml of culture in FIG. 3. It shows the maintenance of the relative abundance of each strain in the consortium during the fermentation process (FIG. 3), showing that strains are represented at deferential levels depending on their trophic function and no strain is washed out during continuous fermentation. The stable metabolic profile of the bioreactor is thus shown to be a valid readout for the maintenance of all strains.

It follows, that despite differential growth rates, the trophic interaction of an intestinal consortium allows a long term and robust continuous fermentation.

TABLE 2

| Name *) | Sequence 5'-3' **) | Orientation of the Primer on 16S rRNA Gene Sequence 5'-3' |
|---|---|---|
| 518R [5] | ATTAC CGCGG CTGCT GG (SEQ ID NO. 21) | Reverse |
| 1392R [1] | ACGGG CGGTG TGTRC (SEQ ID NO. 22) | Reverse |
| 1412R [2] | CGGGT GCTNC CCACT TTCAT G (SEQ ID NO. 23) | Reverse |
| 1492R [4] | GNTAC CTTGT TACGA CTT (SEQ ID NO. 24) | Reverse |
| 1492R.E [1] | TACGG YTACC TTGTT ACGAC TT (SEQ ID NO. 25) | Reverse |
| 1525R [1] | AAGGA GGTGW TCCAR CC (SEQ ID NO. 26) | Reverse |
| F8 [4] | AGAGT TTGAT CMTGG CTC (SEQ ID NO. 27) | Forward |
| F15 [2] | GATTC TGGCT CAGGA TGAAC G (SEQ ID NO. 28) | Forward |
| F27 [1] | AGAGT TTGAT CMTGG CTCAG (SEQ ID NO. 29) | Forward |
| F518 [5] | CCAGC AGCCG CGGTA ATACG (SEQ ID NO. 30) | Forward |

*) sources: 1) Lane, 1991, 2) Kaufmann et al., 1997 4) Mosoni et al., 2007), 5) Muyzer et al., 1993)
**) nucleic codes as defined in IUPAC nucleotide code, particularly: N = any base, R = A or G.

EXAMPLE 5: VIABILITY OF CONSORTIUM

To quantify the total amount of viable cells in the bioreactor, effluent was analyzed using the sybr green, propidium iodide method whereby living cells are stained by sybr green and dead cells by propidum iodine and sybr green allowing the quantification of total viable and dead cells were counted with flow cytometry on 4 consecutive days of fermentation using a Beckman Coulter Cytomics FC 500. Absolute counts are determined with Beckman Coulter Flow-Count Fluorospheres. Cell count in the bioreactor reach over $10^{10}$ viable bacterial cells per ml of culture with a viability of >90%.

It follows that co-culturing allows high density, high viability culturing under continuous fermentation at a retention time of 16 h.

EXAMPLE 6: CONT. VS. BATCH PRODUCTION

To compare production of PB002 through mixing of al 9 strains after separate cultivation to the production of PB002 in a mixed consortium, the metabolic profiles of the two production procedures were tested. PB002 was cultured for 6 days under continuous fermentation conditions as described in example 2. As comparison, the 9 strains were mixed based on their relative proportion in the bioreactor after a 48 h batch culture. Both supernatants of the PB002 produced in the bioreactor by co-culture as well as the mix of the 9 separately cultured strains were compared using HPLC-RI as described above (FIG. 4). Whereby FIG. 4 shows that PB002 produced by continuous fermentation contains exclusively end-metabolites while the strain mix contains 5 mM of lactate and formate as well as traces of succinate. Therefore, the continuous culture of defined and trophically interacting consortia is shown to be an innovative way to produce a life bacterial mix producing exclusively end metabolites at the moment of administration.

EXAMPLE 7: MOUSE MODEL/EFFICACY TESTING

In order to test the potential of PB002 to be used as a replacement of FMT, PB002 was compared to FMT on an acute DSS (dextran sodium sulfate) mouse model. This is a well accepted model for dysbiosis, causing colitis. To induce acute colitis, 12-15 weeks old C57/B6 mice were treated with 3% DSS in drinking water for 7 days. The DSS induced intestinal barrier rupture leads to increased severe diarrhea, intestinal inflammation and consecutive weight loss (expressed in % of initial weight at day 1 of every group in FIG. 5). After 5-7 days of having access to normal drinking water, mice recover spontaneously and return from their dysbiotic, inflammatory state to normal weight. This model of dysbiosis was used to compare the effect of fecal microbiota transplant (of human origin) to the treatment with PB002 continuously cultured as a consortium.

To compare PB002 to human FMT, a microbiota transplant control was used. For fecal transplantation experiments, a fecal suspension was prepared from a healthy donor and stored at −80° C. until usage based on the successfully applied protocol by Youngster and colleagues (Youngster et al. 2014).

To rule out that only bacterial metabolites, products and/or debris account for the effect of the bacterial consortia, fermenter effluent was used as control. Therefore, bacterial suspension from the fermenter was sampled, immediately centrifuged at 14.000-xg for 15 minutes, filtered through a 0.45 μm filter to remove remaining bacteria and larger components and subsequently used as material for transplantation.

Next, it was ruled out that a mix of the same bacteria could be as effective as the consortium grown under co-culture. Therefore, all consortium strains were cultured separately and mixed in the same ratio as the fermenter and maintained under anaerobiosis until transplantation.

All treatment groups were gavaged on 3 consecutive days (day 8, 9 and 10) with 200 μl of the respective suspensions. Groups of 4-5 mice were made separated into
- control group that was not exposed to DSS ( ),
- the untreated DSS group ( ),
- the group treated with PB002 ( ), (inventive)
- the group treated with the mix of independently cultured strains ( ),
- the group treated with the filtered supernatant of PB002 ( ), and
- the group treated with human fecal microbiome transplant (FMT) ( ).

Weight was measured daily until sacrifice on day 16. Mice treated with PB002 showed faster weight recovery starting at the third day of treatment compared to FMT that showed recovery starting one day later and the other treatment groups containing the mix of separately cultured bacteria and the filtered effluent of the continuously cultured PB002 which both did not significantly differ from the untreated DSS control. The presented data therefore show that PB002 when co-cultured continuously can restore a dysbiotic microbiota at least as efficient as FMT. It further shows that co-culturing is a key conditioning for efficacy of the bacterial mix.

Moreover, efficacy of PB002 was confirmed in a different genetic background using BALB/c mice (Table 3). PB002 was compared to FMT in an acute DSS (dextran sodium sulfate) mouse model as described above, whereby DSS was applied at a concentration of 3%. The severity of colitis was quantified by AUC (Area under curve) for negative body weight change (%) per treatment group over the course of the experiment. The AUC summarizes the relative body weight loss over time, quantifying the course of disease of the colitis with increasing AUC for increasing colitis severity.

PB002 showed to accelerate recovery from DSS-induced colitis at least as efficient as FMT (Table 3).

TABLE 3

| Validation of PB002 in a acute DSS BALB/c model | | |
| --- | --- | --- |
| Mouse group | AUC (negative peak) | SD |
| DSS | 70.18 | 9.20 |
| PB002 | 45.46 | 7.32 |
| FMT | 85.45 | 15.28 |

EXAMPLE 8: MOUSE MODEL/INFLAMMATORY PARAMETERS

Besides body weight, the colon length (FIG. 6) as well as the spleen weight (FIG. 7) were quantified for each C57/B6 mouse as measures of inflammation whereby the colon length decreases in case of inflammation and the spleen weight increases upon inflammation. Mice treaded with PB002 showed a highly significant increase of colon length and decrease of spleen weight at least equivalent to the treatment with FMT. The control groups treated with the mix of separately cultured strains as well as the group treated with the filtered supernatant of PB002 did not show significant changes as compared to the DSS treatment group. This experiment shows that treatment with PB002 significantly alleviates inflammation and the immune reaction of the mice, not only normalizing digestion and energy recovery but also the colitis causing inflammatory factors.

EXAMPLE 9: MOUSE MODEL/HISTOLOGY

The inflammatory status of C57/B6 mice was further analyzed by histology of the cecum and of the colon. Staining and histological assessment of colitis severity was performed on formalin-fixed, paraffin embedded samples of the most distal 1.5 cm of the colon and the distal part of the cecum were cut into 5 µm sections and H&E stained according to standard procedures. The slides were analyzed using an AxioCam HRc (Zeiss, Jena, Germany) on a Zeiss Axio Imager.Z2 microscope (Zeiss) and images captured using the AxioVision Release 4.8.2 software (Zeiss). For assessment of colitis severity, the following score was applied: score for epithelial damage: 0, normal morphology; 1, loss of goblet cells; 2, loss of goblet cells in large areas; 3, loss of crypts; 4, loss of crypts in large areas. Score for infiltration: 0, no infiltrate; 1, infiltrate around crypt base; 2, infiltrate reaching to $L.$ $muscularis$ mucosae; 3, extensive infiltration reaching the $L.$ $muscularis$ and thickening of the mucosa with abundant oedema; 4, infiltration of the $L.$ $submucosae$. The total histological score represents the sum of the scores for epithelial damage and infiltration. Histological examination was performed in a blinded manner. Histological analysis of the cecum and colon were performed and quantified for infiltration and epithelial damage by histology score. Representative histology cuts are depicted in FIG. 8 for the cecum and 9 for the colon. Both sections showed significant recovery of the inflammation in the epithelium as compared to the untreated control for PB002 and the benchmark treatment FMT while neither strain mix nor the filtered effluent of PB002 showed significant effects on the DSS colitis.

It follows that PB002, if co-cultured and administered as a suspension of life bacteria and their metabolites, accelerates the healing of epithelial damage and reduces infiltration of the epithelium with immune cells.

EXAMPLE 10: STABILIZING FORMULATION

To compare the efficacy of a cryo-stabilized formulation of PB002 to a consortium applied directly from continuous fermentation, the effluent of the continuously fermented consortium of PB002 was anaerobically mixed 1:1 with an anaerobic cryoprotective medium containing 60% glycerol and 40% of the cultivation medium previously described in example 2. The cryoprotected formulation was snap frozen in liquid nitrogen and stored at −20° C. for at least 1.5 months.

Efficacy of cryo-stabilized PB002 was compared to FMT on an acute DSS (dextran sodium sulfate) mouse model on two different mouse strains, C57BL/6 and BALB/c.

Viability of the stored and fresh formulations were quantified at the moment of administration by flow cytometry as described in example 5. Efficacy of PB002 was shown for viabilities of at least 20%.

The severity of colitis was quantified by AUC (Area under curve) for negative body weight change (%) per treatment group over the course of the experiment.

It follows that cryo-stabilized PB002 successfully accelerated recovery from DSS-induced colitis in two genetic backgrounds when compared to FMT (Table 3, 4).

TABLE 4

Validation of cryo-protected formulation of PB002 on the acute DSS model using C57BL/6 mice

| Mouse group | Rel. Concentration of viable bacteria in sample [%] | SD | AUC (Negative Peak) | SD |
|---|---|---|---|---|
| DSS |  |  | 61.65 | 15.15 |
| PB002 frozen | 88.74 | 1.53 | 31.18 | 5.62 |
| FMT | 41.43 | 0.52 | 68.57 | 13.40 |

TABLE 5

Validation of cryo-protected formulation of PB002 on the acute DSS model using BALB/c mice

| Mouse group | Rel. Concentration of viable bacteria in sample [%] | SD | AUC (Negative Peak) | SD |
|---|---|---|---|---|
| DSS |  |  | 70.18 | 9.20 |
| PB002 frozen | 23.91 | 1.20 | 9.95 | 5.67 |
| FMT | 27.82 | 0.36 | 85.46 | 15.28 |

Throughout this specification, the following references are cited:

Bryant, M. P. (1972). Commentary on the Hungate technique for culture of anaerobic bacteria. The American Journal of Clinical Nutrition, 25(12), 1324-8.

Duncan, S. H., Hold, G. L., Harmsen, H. J. M., Stewart, C. S., & Flint, H. J. (2002). Growth requirements and fermentation products of *Fusobacterium prausnitzii*, and a proposal to reclassify it as *Faecalibacterium prausnitzii* gen. nov., comb. nov. International Journal of Systematic and Evolutionary Microbiology, 52(6), 2141-2146.

Kaufmann, P., Pfefferkorn, A., Teuber, M., & Meile, L. (1997). Identification and quantification of *Bifidobacterium* species isolated from food with genus-specific 16S rRNA gene-targeted probes by colony hybridization and PCR. Applied and Environmental Microbiology, 63(4), 1268-73.

Lane, D. J. (1991). 16S/23S rRNA Sequencing. In E. Stackebrandt & M. Goodfellow (Eds.), Nucleic Acid Techniques in Bacterial Systematics (Chapter 6 pp. 115-148). Sussex: John Wiley and Sons.

Leclerc, M., Bernalier, A., Donadille, G., & Lelait, M. (1997). H2/CO2 metabolism in acetogenic bacteria isolated from the human colon. Anaerobe, 3(5), 307-15.

Lopez-Siles, M., Khan, T. M., Duncan, S. H., Harmsen, H. J. M., Garcia-Gil, L. J., & Flint, H. J. (2012). Cultured representatives of two major phylogroups of human colonic *Faecalibacterium prausnitzii* can utilize pectin, uronic acids, and host-derived substrates for growth. Applied and Environmental Microbiology, 78(2), 420-8.

Maeda, H., Fujimoto, C., Haruki, Y., Maeda, T., Kokeguchi, S., Petelin, M., Takashiba, S. (2003). Quantitative real-time PCR using TaqMan and SYBR Green for *Actinobacillus actinomycetemcomitans, Porphyromonas gingivalis, Prevotella intermedia*, tetQ gene and total bacteria. FEMS Immunology and Medical Microbiology, 39(1), 81-86.

Mosoni, P., Chaucheyras-Durand, F., Béra-Maillet, C., & Forano, E. (2007). Quantification by real-time PCR of cellulolytic bacteria in the rumen of sheep after supplementation of a forage diet with readily fermentable carbohydrates: effect of a yeast additive. Journal of Applied Microbiology, 103(6), 2676-85.

Muyzer, G., de Waal, E. C., & Uitterlinden, A. G. (1993). Profiling of complex microbial populations by denaturing gradient gel electrophoresis analysis of polymerase chain reaction-amplified genes coding for 16S rRNA. Applied and Environmental Microbiology, 59(3), 695-700.

Wang, R. F., Cao, W. W., & Cerniglia, C. E. (1996). PCR detection and quantitation of predominant anaerobic bacteria in human and animal fecal samples. Applied and Environmental Microbiology, 62(4), 1242-7.

Zihler, A., Fuentes, S., Dostal, A., Payne, A. N., Vazquez Gutierrez, P., Chassard, C., . . . Lacroix, C. (2013). Novel Polyfermentor Intestinal Model (PolyFermS) for Controlled Ecological Studies: Validation and Effect of pH. PloS One, 8(10).

Ritari, J., Salojärvi, J., Lahti, L., & de Vos, W. M. (2015). Improved taxonomic assignment of human intestinal 16S rRNA gene sequences by a dedicated reference database. BMC Genomics, 16(1056)

Chassard, C. & Lacroix, C., 2013. Carbohydrates and the human gut microbiota. Current opinion in clinical nutrition and metabolic care, 16(4), pp. 453-460.

The invention claimed is:

1. A composition comprising viable, live bacteria strains (i), intermediate metabolites (ii), end metabolites (iii) and a dispersing medium (iv), characterized in that said bacteria strains (i) being selected from:
   (A1) strains consuming sugars, fibers, and resistant starch, producing formate and acetate, and being selected from the genera *Ruminococcus, Dorea* and *Eubacterium;*
   (A2) strains consuming sugars, starch and acetate, producing formate and butyrate, and being selected from the genera *Faecalibacterium, Roseburia* and *Anaerostipes;*
   (A3) strains consuming sugars and oxygen, producing lactate, and being selected from the genera *Lactobacillus, Streptococcus, Escherichia, Lactococcus* and *Enterococcus;*
   (A4) strains consuming sugars, starch, and carbon dioxide, producing lactate, formate and acetate, and being selected from the genus *Bifidobacterium;*
   (A5) strains consuming lactate or proteins, producing propionate and acetate, and being selected from the genera *Clostridium, Propionibacterium, Veillonella* and *Megasphaera;*
   (A6) strains consuming lactate and starch, producing acetate, butyrate and hydrogen, and being selected from the genera *Eubacterium, Clostridium* and *Anaerostipes;*
   (A7) strains consuming sugar, starch, formate producing lactate, formate and acetate, and being selected from the genus *Collinsella;*
   (A8) strains consuming succinate, producing propionate and acetate, and being selected from the genera *Phascolarctobacterium* and *Dialister;* and
   (A9) strains consuming sugars, fibers, formate and hydrogen, producing acetate and butyrate and being selected from the genera *Acetobacterium, Blautia, Clostridium, Moorella, Methanobrevibacter, Methanomassiliicoccus* and *Sporomusa;*
   wherein said bacteria strains are in each case identified through classification of the full 16S gene with assignment for the different taxonomic levels Phylum: 75%, Class: 78.5%, Order: 82%, Family: 86.5%, Genus: 94.5%, sequence similarity;
   wherein one or more bacteria strain from all nine groups (A1) to (A9) are present;
   wherein said bacteria strains (i) being present in a total concentration of over $10^9$ bacteria per ml composition; and
   wherein said bacteria strains (i) having a viability of over 50% as determined by flow cytometry; and
   said intermediate metabolites (ii) being selected from:
   succinate in an amount of less than 5 mM,
   formate in an amount of less than 5 mM, and
   lactate in an amount of less than 5 mM; and
   said end metabolites (iii) being selected from
   acetate in an amount of at least 10 mM,
   propionate in an amount of at least 2 mM, and
   butyrate in an amount of at least 2 mM; and
   said dispersing medium (iv) being selected from:
   culture media,
   cryoprotecting media,
   aqueous gels, and
   polymeric supports.

2. The composition of claim 1, characterized in that each of said viable, live bacteria strains (i) being present in an amount of $10^5$-$10^{14}$ 16S rRNA gene copies per ml, as quantified by qPCR.

3. The composition of claim 1, characterized in that said viable bacteria strains (i)

(A1) are selected from *Ruminococcus bromii, Ruminococcus lactaris, Ruminococcus champanellensis, Ruminocccus callidus, Ruminococcus gnavus, Ruminococcus obeum, Dorea longicatena, Dorea formicigenerans* and *Eubacterium eligens*;

(A2) are selected from *Faecalibacterium prausnitzii, Anaerostipes hadrus, Roseburia intestinalis*;

(A3) are selected from *Lactobacillus rhamnosus, Streptococcus salivarius, Escherichia coli, Lactococcus lactis* and *Enterococcus caccae*;

(A4) are selected from *Bifidobacterium adolescentis, Bifidobacterium angulatum, Bifidobacterium bifidum, Bifidobacterium breve, Bifidobacterium catenulatum, Bifidobacterium dentium, Bifidobacterium gallicum, Bifidobacterium longum, Bifidobacterium pseudocatenumlatum*;

(A5) are selected from *Clostridium aminovalericum, Clostridium celatum, Clostridium lactatifermentans, Clostridium neopropionicum, Clostridium propionicum, Megasphaera elsdenii, Veillonella montpellierensis* and *Veillonella ratti*;

(A6) are selected from *Anaerostipes caccae, Clostridium indolis, Eubacterium hallii, Eubacterium limosum, Eubacterium ramulus*;

(A7) are selected from *Collinsella aerofaciens, Collinsella intestinalis, Collinsella stercoris*;

(A8) are selected from *Phascolarctobacterium faecium, Dialister succinatiphilus* and *Dialister propionifaciens*; and (A9) are selected from *Acetobacterium carbinolicum, Acetobacterium malicum, Acetobacterium wieringae, Blautia hydrogenotrophica, Blautia producta Clostridium aceticum, Clostridium glycolicum, Clostridium magnum, Clostridium mayombei, Methanobrevibacter smithii* and *Candidatus Methanomassiliicoccus intestinalis*.

4. The composition according to claim 1, wherein dispersing medium (iv) is selected from:
Cryoprotecting media comprising glycerol; and/or
Culture media comprising fibres, proteins, co-factors, vitamins, and reducing agents.

5. The composition of claim 1, characterized in that said bacteria strains (A1) to (A9) are obtained by co-cultivation.

6. The composition according to claim 5, wherein the co-cultivation is at a pH 5.5-6.5 under inert atmosphere.

7. The composition according to claim 1, for use in the prophylaxis, treatment, prevention or delay of progression of a disease associated with intestinal microbiome dysbalance or associated with microbiota dysbiosis.

8. The composition according to claim 7, wherein said disease is selected from *Clostridium difficile* infection (CDI), vancomycin resistant enterococci (VRE), intestinal infections, post-infectious diarrhea, inflammatory bowel diseases (IBD).

9. The composition according to claim 1, wherein said bacteria strains have a viability of over 70%.

10. The composition of claim 1, which is a pharmaceutical composition.

11. The pharmaceutical composition of claim 10, which is free of, or essentially free of, other viable, live bacteria; and/or
free of, or essentially free of, succinate, formate and lactate.

12. The pharmaceutical composition according to claim 10, further comprising a culture medium and/or a cryoprotecting medium.

13. The pharmaceutical composition according to claim 10, which is
adapted to rectal administration, or
adapted to oral administration.

14. A composition comprising co-cultivated viable, live, human, intestinal bacteria strains (A1) to (A9) as defined in claim 1, for use as a pharmaceutical.

15. A method for manufacturing a composition according to claim 1, said method comprising the steps of:
(a) providing a composition comprising viable, live bacteria strains (A1)-(A9) as defined in claim 1;
(b) cultivating the composition of step (a) to obtain a composition in the form of a suspension; and
(c) optionally post treatment steps;
characterized in that the cultivation of step (b) is a continuous co-cultivation.

16. The method of claim 15, characterized in that step (a) comprises the steps of:
(a1) providing and separately cultivating said bacteria strains (A1)-(A9) in the presence of a substrate specific for each of said strains (A1)-(A9);
(a2) combining and co-cultivating the materials obtained in (a1) in the presence of a substrate comprising amicase, yeast extract, arabinogalactan, fructo-oligosaccharides, soluble starch, resistant starch, xylan, at a pH 5.5-6.5 and an inert atmosphere;
characterized in that step (a2) is performed batch-wise and is terminated once metabolites succinate, formate and lactate are each below 5 mM.

17. The method according to claim 15, wherein in step (b) the mixture of strains (A1)-(A9) is continuously cultivated in the presence of a substrate comprising amicase, yeast extract, arabinogalactan, fructo-oligosaccharides, soluble starch, resistant starch, xylan, at a pH 5.5-6.5 and an inert atmosphere.

18. The method according to claim 15, wherein in step (c) the suspension obtained from step (b) is combined with a cryoprotectant.

* * * * *